United States Patent
Kramer et al.

(10) Patent No.: US 9,573,883 B2
(45) Date of Patent: Feb. 21, 2017

(54) SALTS OF CARNITINE DERIVATIVES AND METHODS OF PRODUCTION

(71) Applicant: ThermoLife International, LLC, Phoenix, AZ (US)

(72) Inventors: Ronald Kramer, Phoenix, AZ (US); Alexander Nikolaidis, New Kallikratia (GR)

(73) Assignee: ThermoLife International, LLC, Chandler, AZ (US)

( * ) Notice: Subject to any disclaimer, the term of this patent is extended or adjusted under 35 U.S.C. 154(b) by 0 days.

(21) Appl. No.: 14/570,748

(22) Filed: Dec. 15, 2014

(65) Prior Publication Data
US 2015/0166466 A1 Jun. 18, 2015

(30) Foreign Application Priority Data
Dec. 16, 2013 (CN) .......................... 2013 1 0682868

(51) Int. Cl.
*C07C 229/22* (2006.01)
*C07C 227/42* (2006.01)
*C07C 227/16* (2006.01)

(52) U.S. Cl.
CPC .................................. *C07C 229/22* (2013.01)

(58) Field of Classification Search
CPC ..... C07C 229/22; C07C 227/16; C07C 227/42
See application file for complete search history.

(56) References Cited

U.S. PATENT DOCUMENTS

| 8,003,683 B2 * | 8/2011 | Chandran ............. A23L 1/3051 514/423 |
| 2009/0137670 A1 | 5/2009 | Kramer et al. |

FOREIGN PATENT DOCUMENTS

| CN | 103664667 | 3/2014 |
| WO | 2015095236 | 6/2015 |

OTHER PUBLICATIONS

Sakami et al. Journal of Biological Chemistry, (1942), V.144, p. 203-216.*
Bohmer, Thomas et al. Propionylcarnitine physiological variations in vivo. Biochimica et Biophysica Acta, 1968, 152, pp. 559-567, p. 560, lines 7-22.
Bohmer, T. et al., Propionylcarnitine physiological variations in vivo. Biochim. Biophys. Acta, 1968, 152, pp. 559-567.

* cited by examiner

*Primary Examiner* — Yong Chu
(74) *Attorney, Agent, or Firm* — Booth Udall Fuller, PLC

(57) ABSTRACT

Disclosed are salts, such as nitrates, of acetyl-L-carnitine and propionyl-L-carnitine and methods of making the compounds.

28 Claims, No Drawings

SALTS OF CARNITINE DERIVATIVES AND METHODS OF PRODUCTION

CROSS-REFERENCE TO RELATED APPLICATIONS

The present application claims priority to Chinese Patent Application No. CN201310682868 filed Dec. 16, 2013, which is hereby incorporated by reference in its entirety.

TECHNICAL FIELD

Aspects of this document relate generally to acyclic organic compounds substituted with a carboxylic acid group, such as acetyl-L-carnitine and propionyl-L-carnitine, and more specifically to salts of carnitine derivatives and methods of production.

BACKGROUND

Carnitine is a quaternary ammonium compounds synthesized from the amino acids lysine and methionine. In eukaryotes, carnitine is required for the transport of fatty acids from the intermembraneous space of the mitochondria into the mitochondrial matrix during the breakdown of lipids for the generation of metabolic energy. In animals, biosynthesis of carnitine primarily occurs in the liver and kidneys. However, carnitine may also be absorbed in the diet, primarily from red meats, but also in significantly lower levels in many other foods, such as, nuts and seed, legumes, vegetables, fruits, and cereals. Although carnitine naturally occurs in two stereoisomers, only the L-enantiomer is biologically active. The efficacy of L-carnitine has been reported for numerous applications. It is an important dietary/nutritional supplement. L-carnitine has been widely used in the food industry and may also be therapeutically effective.

Acetyl-L-carnitine and propionyl-L-carnitine are derivatives of L-carnitine that are naturally produced in the body. For example, during strenuous exercise, L-carnitine and used acetyl-CoA are converted into acetyl-L-carnitine and CoA by carnitine acetyltransferase inside the mitochondria. Acetyl-L-carnitine is then transported outside of mitochondria and converted back to L-carnitine, for example, by plasma esterases in the blood, before it is cycled back into the mitochondria for transporting of fatty acid. The mechanism of propionyl-L-carnitine biosynthesis is similar to that of acetyl-L-carnitine. Instead of converting L-carnitine and acetyl-CoA, carnitine acetyltransferase converts L-carnitine and propionyl-CoA in the mitochondria into propionyl-L-carnitine and CoA.

Both acetyl-L-carnitine and propionyl-L-carnitine are believed to have many advantageous properties over L-carnitine, such as increased bioavailability. For example, researchers prefer to use acetyl-L-carnitine to study the effects of carnitine in the body, because it has better absorption than L-carnitine in the small intestine and is more able to cross the blood/brain barrier.

Notwithstanding, the typical method of production for propionyl-l-carnitine and acetyl-l-carnitine involves the reaction of propionyl chloride and acetyl chloride respectively. During the reaction the end product would be propionyl-l-carnitine/acetyl-l-carnitine which would readily react with the hydrochloric acid formed by the reaction to wield the respective hydrochloride salts (acetyl-l-carnitine hydrochloride and propionyl-l-carnitine hydrochloride). Being a strong inorganic acid, HCl is practically impossible to replace with nitric acid and other acids to achieve nitrate and other salts of acetyl and propionyl l-carnitine. Thus, to this day, acetyl and propionyl carnitine are offered only as hydrochloride salts for sale and use in the supplement industry.

SUMMARY

The present disclosure provides new methods of producing salts of L-carnitine derivatives, such as acetyl-L-carnitine and propionyl-carnitine. While L-carnitine and its derivatives are already sold as dietary supplements, it is still desirable to have new carnitine compounds and compositions that have properties lacking in conventional carnitine, conventional L-carnitine derivatives, conventional nitrates, and/or the like alone.

One aspect of this disclosure provides for compounds comprising the chemical formula:

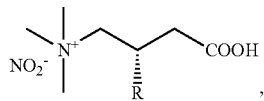

wherein R is selected from the group consisting of: acetyl group and propionyl group.

Another aspect provides for methods of producing such compounds. A method may generally include reacting L-carnitine with an acid anhydride to produce a L-carnitine derivative free base; isolating the L-carnitine derivative free base; reacting the L-carnitine derivative free base with nitric acid to produce nitrate of the L-carnitine derivative; and isolating the nitrate of the L-carnitine derivative.

One embodiment is methods of producing acetyl-L-carnitine nitrate comprising: reacting L-carnitine with acetic anhydride to produce acetyl-L-carnitine free base; isolating the acetyl-L-carnitine free base; reacting the acetyl-L-carnitine free base with nitric acid to produce acetyl-L-carnitine nitrate; and isolating the acetyl-L-carnitine nitrate. Particular implementations of the methods may include one or more of the following. The molar ratio of acetic anhydride to L-carnitine is about 1:1 to 3:1. The molar ratio of nitric acid to acetyl-L-carnitine free base is about 1:1 to 1.5:1. In some implementations, reacting L-carnitine with acetic anhydride to produce acetyl-L-carnitine free base comprises dissolving the L-carnitine in acetic acid, and the reaction between L-carnitine and acetic anhydride occurs at a temperature of between 30° C. and 80° C. the reaction may occur for 3 to 12 hours. The ratio of acetic acid to L-carnitine is about 0.65 g to 3 g acetic acid for every gram of L-carnitine.

In some implementations of the methods of producing acetyl-L-carnitine nitrate, isolating the acetyl-L-carnitine nitrate comprises: distilling the reaction of acetyl-L-carnitine free base and nitric acid to remove the other products of the reaction; washing the acetyl-L-carnitine nitrate with acetone; and crystallizing the acetyl-L-carnitine nitrate. Particular implementations of the method may include one or more of the following. Washing the acetyl-L-carnitine nitrate with acetone comprises using an amount of acetone by weight that is two to five times the amount acetyl-L-carnitine free base by weight. Crystallizing the acetyl-L-carnitine nitrate comprises cooling the acetyl-L-carnitine nitrate to below 5° C. In some aspects, crystallizing acetyl-L-carnitine nitrate further comprises maintaining the acetyl-L-carnitine nitrate at between 0° C. and 5° C. for at least 2 hours.

In one implementation of methods of producing acetyl-L-carnitine nitrate, the method may begin by first producing acetyl-L-carnitine and then producing acetyl-L-carnitine nitrate from the produced acetyl-L-carnitine. The step of producing acetyl-L-carnitine comprises adding L-carnitine to a reactor and then dissolving it with acetic acid. Then acetic anhydride is added to the reactor and the contents are allowed to react for three to 12 hours. Acetic acid produced from the reaction of acetic anhydride and dissolved L-carnitine is removed by distilling the contents of the reactors under reduced pressure. The remaining contents of the reactors are then stirred with acetone before cooling to below 5° C. for crystallization. The contents should remain at between 0° C. to 5° C. for at least two hours. The crystallized acetyl-L-carnitine is extracted by filtration followed by drying. The step of producing acetyl-L-carnitine nitrate comprises dissolving the crystallized acetyl-L-carnitine in a reactor with acetic acid and then reacting the acetyl-L-carnitine with nitric acid for two to five hours at 30° C. to 80° C. Water and acetic acid produced from the reaction are removed by distillation under reduced pressure, and the remaining contents are stirred with acetone before cooling to below 5° C. for crystallization. The contents should remain at between 0° C. to 5° C. for at least two hours before the crystallized acetyl-L-carnitine nitrate is extracted by filtration followed by drying.

In some implementations of the step for producing acetyl-L-carnitine, the ratio of acetic acid to L-carnitine in producing acetyl-L-carnitine free base is 0.65 g to 3 g acetic acid for every gram of L-carnitine. In some implementations of the step for producing acetyl-L-carnitine free base, the molar ratio of acetic anhydride to L-carnitine is between 1:1 to 3:1. In some implementations of producing acetyl-L-carnitine nitrate, the ratio of acetic acid to acetyl-L-carnitine free base is 0.8 g to 3 g acetic acid for every gram of acetyl-L-carnitine free base. In some implementations of producing acetyl-L-carnitine nitrate, the molar ratio of nitric acid to acetyl-L-carnitine free base is between 1:1 to 1.5:1. In some implementations, for both producing acetyl-L-carnitine free base and acetyl-L-carnitine nitrate, the amount of acetone used by weight is two to five times the amount of L-carnitine or acetyl-L-carnitine free base, respectively, by weight.

Another embodiment is methods of producing propionyl-L-carnitine nitrate comprising: reacting L-carnitine with propionic anhydride to produce propionyl-L-carnitine free base; isolating the propionyl-L-carnitine free base; reacting the propionyl-L-carnitine free base with nitric acid to produce propionyl-L-carnitine nitrate; and isolating the propionyl-L-carnitine nitrate. In some implementations, the molar ratio of propionic anhydride to L-carnitine is about 1.5:1. Particular implementations may include one or more of the following.

In some implementations, reacting L-carnitine with propionic anhydride to produce propionyl-L-carnitine free base further comprises mixing the L-carnitine with potassium hydroxide, wherein the reaction of L-carnitine, potassium hydroxide, and propionic anhydride occurs at a temperature of about 80° C. In some aspects, the molar ratio of L-carnitine and potassium hydroxide may be 1:1. In some implementations a method of producing propionyl-L-carnitine nitrate, a small amount of pyridine is added to the reaction of L-carnitine, potassium hydroxide, and propionic anhydride as a catalyst. In this implementation, the reaction of L-carnitine, potassium hydroxide, and propionic anhydride occurs for between 1 to 3 hours.

In some implementations, the reaction between the propionyl-L-carnitine free base with nitric acid occurs at about 30° C. The reaction between the propionyl-L-carnitine free base and nitric acid may occur for about 2 hours.

In some implementations, isolating the propionyl-L-carnitine nitrate comprises crystallizing the propionyl-L-carnitine nitrate by drying the reaction between the propionyl-L-carnitine free base and nitric acid. The reaction between the propionyl-L-carnitine free base and nitric acid may be dried in a vacuum.

In some implementations, isolating the propionyl-L-carnitine comprises: filtering the reaction of L-carnitine and propionic anhydride to discard the precipitate; and crystallizing the propionyl-L-carnitine free base. In some aspects, crystallizing the propionyl-L-carnitine free base comprises cooling the solution product of the reaction of L-carnitine and propionic anhydride to between 0° C. and 5° C.

All of the foregoing and other implementations of salts, such as nitrates, of acetyl-L-carnitine and propionyl-L-carnitine and methods of making the compounds may include or exhibit one or more of the following benefits and advantages.

For example, acetyl-L-carnitine nitrate, whose methods of production are reported for the first time in this disclosure, is more stable, and is more suitable for storage, transport, and preparation of solid products. The disclosed methods of producing acetyl-L-carnitine nitrate include a simple, low-cost, method that is suitable for industrial scale production of acetyl-L-nitrate. Because the methods do not use catalysts, the products are more easily purified or isolated. The methods also have short reaction times, high product quality and yield, and high production efficiency. Additionally, the acetic acid and acetone used in the reaction may be recovered, which reduces solvent waste and results in production costs savings.

Nitrates of acetyl-L-carnitine and propionyl-L-carnitine also have wider uses in the supplement industry. Acetyl-L-carnitine hydrochloride and propionyl-L-carnitine hydrochloride salts are source and bitter tasting, which would not be suitable for certain forms of dietary supplements where the subject would be able to taste the salts. In contrast, nitrates taste better. Thus acetyl-L-carnitine nitrate and propionyl-L-carnitine are suitable for use in chewable tablets, gummies, or nutrition bars and drinks including sports drinks.

The foregoing and other aspects, features, and advantages will be apparent to those of ordinary skill in the art from the DESCRIPTION and the CLAIMS.

DETAILED DESCRIPTION OF THE INVENTION

Overview

There are many features of implementations of salts of carnitine derivatives and methods of production disclosed herein, of which one, a plurality, or all features or steps may be used in any particular implementation. In the following description, for the purposes of explanation, numerous specific details are set forth in order to provide a thorough understanding of the present disclosure. It will be apparent, however, to one skilled in the art that the present disclosure is not so limited. It is also to be understood that other implementations may be utilized, and structural, as well as procedural, changes may be made without departing from the scope of this document. As a matter of convenience, various compounds and methods will be described. However, this document is not limited to the stated examples and other compounds and methods are possible and within the teachings of the present disclosure.

As used herein, the verbs "comprise" and "include" as used in this description and in the claims and their conjugations are used in their non-limiting sense to mean that items following the words are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

"Compound" is a term used herein in its broadest sense and may refer to a chemical substance comprising two or more different chemically bonded chemical constituent elements or ingredients, with a fixed ratio or proportion by weight. The term compound may specifically refer to a compound encompassed by the generic formulae disclosed herein, any subgenus of those generic formulae, and any forms of the compounds specified by the generic and subgeneric formulae. The atoms within a compound can be held together by a variety of interactions, ranging from covalent bonds to electrostatic forces in ionic bonds. The physical and chemical properties of compounds are different from those of their constituent elements. This is one of the main criteria for distinguishing a compound from a mixture of elements or other substances because a mixture's properties are generally closely related to and dependent on the properties of its constituents. However, some mixtures are so intimately combined that they have some properties similar to compounds. Another criterion for distinguishing a compound from a mixture is that the constituents of a mixture can usually be separated by simple, mechanical means such as filtering, evaporation, or use of a magnetic force, but the components of a compound can only be separated by a chemical reaction. Conversely, mixtures can be created by mechanical means alone, but a compound can only be created (either from elements or from other compounds, or a combination of the two) by a chemical reaction. Unless specified otherwise, the term compound further includes the isotopes, racemates, solvates, stereoisomers, and tautomers of the compound.

As used herein, "composition" is a term used in its broadest sense and may refer to a mixture of constituent substances or ingredients.

As used here in, "mixture" is a term used in its broadest sense and may refer to two or more constituent substances or ingredients (chemical species present in a system), which have been combined (not necessarily in fixed proportions and not necessarily with chemical bonding and not necessarily so that each substance retains its own chemical identity). Mixtures can be the product of a blending or mixing of chemical substances like elements and compounds, without chemical bonding or other chemical change, so that each ingredient substance retains its own chemical properties and makeup. Mixtures can be either homogeneous or heterogeneous. A homogeneous mixture is a type of mixture in which the composition is uniform. A heterogeneous mixture is a type of mixture in which the composition can easily be identified, as there are two or more phases present. A homogeneous mixture in which there is both a solute and solvent present is also a solution.

As used herein, "acceptable additive" or "additive" are terms used in their broadest sense. Particular implementations of the compositions described in this document may also comprise an additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof). These additives may be solids or liquids, and the type of additive may be generally chosen based on the type of administration being used. Those of ordinary skill in the art will be able to readily select suitable effective additives from the disclosure in this document. In particular implementations, acceptable additives may include, by non-limiting example, calcium phosphate, cellulose, stearic acid, croscarmellose cellulose, magnesium stearate, and silicon dioxide.

As used in this document, "effective" is a phrase used in its broadest sense, including, by non-limiting example, effective in a clinical trial, for a specific patient, or only placebo-effective. As used herein, an "effective amount," an "amount effective for," or "amount sufficient to" is defined as an amount effective, at dosages and for periods of time necessary, to achieve a desired biological result, such as reducing, preventing, or treating a disease or condition and/or inducing a particular beneficial effect. The effective amount of compounds and compositions of the disclosure may vary according to factors such as age, sex, and weight of the individual. Dosage regime may be adjusted to provide the optimum response. Several divided doses may be administered daily, or the dose may be proportionally reduced as indicated by the exigencies of an individual's situation. As will be readily appreciated, a composition in accordance with the present disclosure may be administered in a single serving or in multiple servings spaced throughout the day. As will be understood by those skilled in the art, servings need not be limited to daily administration, and may be on an every second or third day or other convenient effective basis. The administration on a given day may be in a single serving or in multiple servings spaced throughout the day depending on the exigencies of the situation.

As used in this document, "acceptable" is a phrase used in its broadest sense and may describe ingredients of a composition that meet Food and Drug Administration (FDA) standards, United States Pharmacopeial Standards (USP), US Department of Agriculture (USDA) standards for food-grade materials, commonly accepted standards of the nutritional supplement industry, industry standards, botanical standards, or standards established by any individual. These standards may delineate acceptable ranges of aspects of ingredients of a composition such as edibility, toxicity, pharmacological effect, or any other aspect of a chemical, composition, or preparation used in implementations of a composition.

Prior to this disclosure, only hydrochloride salts of acetyl and propionyl-L-carnitine have been produced. The typical method of production for acetyl-L-carnitine and propionyl-L-carnitine involve the reaction of acetyl chloride (Scheme 1) and propionyl chloride (Scheme 2) respectively with L-carnitine. The products, acetyl-L-carnitine and propionyl-L-carnitine, then readily react with the hydrochloric acid also formed by the reaction to produce the respective hydrochloride salts, acetyl-l-carnitine hydrochloride and propionyl-l-carnitine hydrochloride.

Scheme 1.

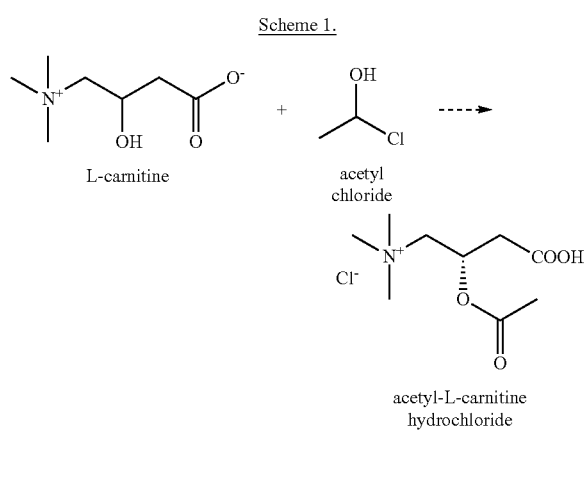

acetyl-L-carnitine
hydrochloride

Scheme 2.

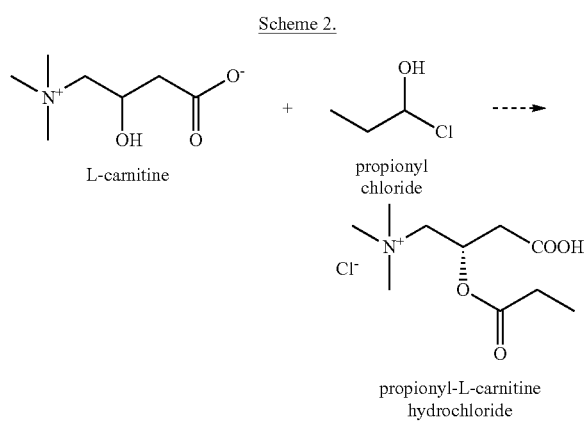

propionyl-L-carnitine
hydrochloride

Because hydrochloric acid is a strong inorganic acid, it is practically impossible to replace it with nitric acid or many other acids.

However, there is a need for a method of producing nitrate and other salts of acetyl- and propionyl-L-carnitine. The nitrate ion enhances absorption of compounds by the intestine. Nitrates increase bioavailability by increasing intestinal absorption of nutrients and increasing vasodilation and blood flow and blood is the carrier of the nutrients to cells.

Also, the nitrate ion can cause vasodilatation after reduction to nitrite and then nitric oxide, improve blood circulation, to the muscles and thus distribution of these compounds to the muscle, as well as oxygen distribution to the muscles. Muscle oxygen is needed to provide energy, which is needed for all muscle anabolic actions to take place as well as for the active transport of above nutrients via the cell membrane. See the following references, which are hereby incorporated herein by reference: Bailey, Stephen G. et al., "Dietary nitrate supplementation reduces the O2 cost of low-intensity exercise and enhances tolerance to high-intensity exercise in humans", PresS. J Appl Physiol (Aug. 6, 2009) and Bailey, Stephen G. et al., "Dietary nitrate supplementation enhances muscle contractile efficiency during knee-extensor exercise in humans", J Appl Physiol 109:135-148, 2010).

In these same references, the nitrate ion's positive effect on athletic endurance and muscle strength is also very well described. Oxygen is needed by the body to produce energy, which by itself is needed for all the metabolic processes in the body, including the generation of metabolic energy. Thus, administration of a nitrate salt of a carnitine derivative would increase the distribution of the carnitine derivative to the muscle and increase its effectiveness. Therefore, not only would the nitrate salt of a carnitine derivative have improved bioavailability, absorption and effectiveness, but also the co-administration of nitrate through another nitrate salt, acid or a natural source of nitrate in a composition of the present disclosure would have similar effects, albeit lower than in the case of nitrate bonded with the molecule.

Description

In one aspect this disclosure provides nitrate salts of L-carnitine derivatives having the chemical structure:

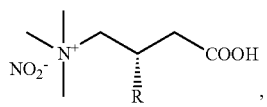

wherein R is an acetyl group or an propionyl group.

In another aspect this disclosure further provides a simple, time-efficient, cost-effective method of producing compounds such as acetyl-L-carnitine nitrate and propionyl-L-carnitine nitrate for example, which is also suitable for industrial mass production. The method may generally include reacting L-carnitine with an acid anhydride to produce derivatives of carnitine as free bases that are then reacted with an acid to produce salts of carnitine derivatives. The organic acids produced from the reaction of L-carnitine with an acid anhydride may optionally be removed by evaporation or reaction with a strong base, for example KOH, to form a solid, which could be removed by filtration. Accordingly, the methods of the invention comprises producing the free base of a carnitine derivative and producing the salt of carnitine derivative from the free base of the carnitine derivative. In some embodiments, the free base of a carnitine derivative must be isolated as crystals prior to the reaction with the acid. In other embodiments, the free base of a carnitine need not be isolated as a crystal prior to the reaction with the acid.

Although the main scope of this disclosure is to produce nitrate salts of L-carnitine derivatives, which offer far superior properties compared to regular L-carnitine derivatives, other nutritionally useful salts of L-carnitine derivatives may be produced by combining the free base of the L-carnitine derivative produced according to the methods of the invention with a respective acid in an appropriate solvent if needed and proceed to evaporate the solvent at a suitable temperature, optionally under vacuum. Suitable acids that may be used to procure the respective salts include but are not limited to: Alpha ketoglutaric acid, malic acid, sulfuric acid, sulfurous acid, ascorbic acid, fumaric acid, tartaric acid, hydrobromic acid, nitric acid, nitrous acid, hyponitrous acid, disulfuric acid, sulfonic acid, phosphoric acid, pyrophosphoric acid, diphosphonic acid, malonic acid, carbonic acid, succinic acid, carbonic acid, bicarbonic acid, acetic acid, propionic acid, beta alanine, aspartic acid, glutamic acid, leucine, valine, isoleucine, glycine, alanine, proline, phenylalanine, tyrosine, tryptophan, serine, threonine, cysteine, creatine, methionine, asparagine, glutamine.

In one embodiment, acetyl-L-carnitine free base is produced by reaction L-carnitine with acetic anhydride, for example at a reaction temperature of between −71° C. to 139.8° C., between 0° C. to between 100° C., or between 30° C. to 80° C. The reaction may be for at least five minutes, for example between 3 to 12 hours. In some implementations, the molar ratio of acetic anhydride to L-carnitine is about 1:1 to 3:1. In some implementations, L-carnitine is first dissolved in acetic acid. In some aspects, the ratio of acetic acid to L-carnitine is between 0.65 to 3 grams of acetic acid for one gram of L-carnitine.

To isolate the acetyl-L-carnitine, the acetyl-L-carnitine free base and acetic acid produced from the reaction between L-carnitine and acetic anhydride is separated by distillation, wherein the acetic acid is distilled away. In some embodiments, the distillation occurs under reduced pressure, for example in a vacuum. The isolated acetyl-L-carnitine free base is then washed with acetone by thoroughly mixing the acetyl-L-carnitine free base and the acetone. In some implementations, the amount of acetone to wash the solution of acetyl-L-carnitine is about two to five times the amount of the L-carnitine. The mixture is then cooled to allow the acetyl-L-carnitine free base to crystallize, for example, at a temperature of below 5° C. In some embodiments, the crystallized acetyl-L-carnitine free base is maintained at a temperature of between 0° C. and 5° C. for at least two hours. The crystallized acetyl-L-carnitine free base is then filtered from acetone and dried before it is used to produce acetyl-L-carnitine nitrate.

In alternative embodiments, acetyl-L-carnitine free base can be purified from the other products of the reaction between L-carnitine and acetic anhydride by evaporation or reaction with a strong base. For example, the excess acetic acid may be removed by evaporation. The excess acetic acid may also be removed in a reaction with a strong base, such as KOH. The reaction with a strong base produces a solid salt that could be removed by filtration.

To produce acetyl-L-carnitine nitrate, the acetyl-L-carnitine free base is reacted with nitric acid at a temperature of between 30° C. and 80° C. In some embodiments, the acetyl-L-carnitine free base and the nitric acid are allowed to react for 2 to 5 hours. In some implementations, the molar ratio of nitric acid to acetyl-L-carnitine free base is about 1:1 to 1.5:1. In some implementations, L-carnitine is first dissolved in acetic acid. In some implementations, the ratio of acetic acid to L-carnitine is between 0.8 g to 3 g acetic acid for one gram of acetyl-L-carnitine free base.

The reaction produces acetyl-L-carnitine nitrate, nitric acid, and excess water, so the nitric acid and water are distilled away, wherein the distillation occurs under reduced pressure, for example, in a vacuum. The acetyl-L-carnitine nitrate is then washed with acetone. For example, acetyl-L-carnitine nitrate is thoroughly mixed with acetone and cooled to below 5° C. to allow the acetyl-L-carnitine nitrates crystals to form. As in the washing of acetyl-L-carnitine free base crystals, in some implementations, the amount of acetone, by weight, to wash the solution of acetyl-L-carnitine nitrate is about two to five times the amount of the acetyl-L-carnitine free base by weight. In some embodiments, the crystallized acetyl-L-carnitine free base is maintained at a temperature of between 0° C. and 5° C. for at least two hours. The crystallized acetyl-L-carnitine crystals is then filtered from acetone and dried.

The advantages of the aforementioned methods of producing acetyl-L-carnitine nitrate include a simple, low-cost, method that is suitable for industrial scale production of acetyl-L-nitrate. Because the methods do not use catalysts, the products are more easily purified or isolated. The methods also have short reaction times, high product quality and yield, and high production efficiency. Additionally, the acetic acid and acetone used in the reaction may be recovered, which reduces solvent waste and results in production costs savings.

In another embodiment, propionyl-L-carnitine free base is produced by reaction L-carnitine with propionic anhydride, for example at a reaction temperature of between −21° C. to 141° C., between 0° C. to 100° C., or between 30° C. to 80° C. In one implementation, L-carnitine and propionic anhydride are reacted at about 30° C. The reaction may be for at least 5 minutes, for example between 3 to 12 hours or between 1 to 3 hours. In some implementations, the molar ratio of propionic anhydride to L-carnitine is about 1:1 to 3:1, for example about 1.5:1. In some implementations, L-carnitine is first dissolved in propionic acid. In some aspects, the ratio of propionic acid to L-carnitine is between 0.75 to 3.3 grams of propionic acid for one gram of L-carnitine.

To isolate the propionyl-L-carnitine free base, the propionyl-L-carnitine free base and propionic acid produced from the reaction between L-carnitine and propionic anhydride may be separated by distillation, wherein the propionic acid is distilled away. In some embodiments, the distillation occurs under reduced pressure, for example in a vacuum. The isolated propionyl-L-carnitine free base is then washed with acetone by thoroughly mixing the propionyl-L-carnitine free base and the acetone. In some implementations, the amount of acetone to wash the solution of propionyl-L-carnitine is about two to five times the amount of the L-carnitine. The mixture is then cooled to allow the propionyl-L-carnitine free base to crystallize, for example, at a temperature of below 5° C. In some embodiments, the crystallized propionyl-L-carnitine free base is maintained at a temperature of between 0° C. and 5° C. for at least two hours. The crystallized propionyl-L-carnitine free base is then filtered from acetone and dried before it is used to produce propionyl-L-carnitine nitrate.

In alternative embodiments, the propionyl-l-carnitine free base may be purified from the excess propionic acid by removal of the excess propionic acid, for example by evaporation or by a reaction with a strong base such as KOH. The reaction of propionic acid with a strong base produces solid salt that may be removed by filtration.

To produce propionyl-L-carnitine nitrate, the propionyl-L-carnitine free base is reacted with nitric acid at a temperature of between 30° C. and 80° C. In some embodiments, the propionyl-L-carnitine free base and the nitric acid are allowed to react for 2 to 5 hours. In some implementations, the molar ratio of nitric acid to propionyl-L-carnitine free base is about 1:1 to 1.5:1. In some implementations, L-carnitine is first dissolved in propionic acid. In some implementations, the ratio of propionic acid to L-carnitine is between 0.9 g to 3.3 g propionic acid for one gram of propionyl-L-carnitine free base.

The reaction produces propionyl-L-carnitine nitrate, nitric acid, and excess water, so the nitric acid and water are distilled away, wherein the distillation occurs under reduced pressure, for example, in a vacuum. The propionyl-L-carnitine nitrate is then washed with acetone. For example, propionyl-L-carnitine nitrate is thoroughly mixed with acetone and cooled to below 5° C. to allow the propionyl-L-carnitine nitrates crystals to form. As in the washing of propionyl-L-carnitine free base crystals, in some implementations, the amount of acetone, by weight, to wash the solution of propionyl-L-carnitine nitrate is about two to five times the amount of the propionyl-L-carnitine free base by weight. In some embodiments, the crystallized propionyl-L-carnitine free base is maintained at a temperature of between 0° C. and 5° C. for at least two hours. The crystallized propionyl-L-carnitine crystals is then filtered from acetone and dried.

Other Implementations

Although the main scope of this disclosure is to produce nitrate salts of L-carnitine derivatives, which offer far superior properties compared to regular L-carnitine derivatives, other nutritionally useful salts of L-carnitine derivatives may be produced by combining the free base of the L-carnitine derivative produced according to the methods of this disclosure with a respective acid in an appropriate solvent if needed and proceed to evaporate the solvent at a suitable temperature, optionally under vacuum. Suitable acids that may be used to procure the respective salts include but are not limited to: Alpha ketoglutaric acid, malic acid, sulfuric acid, sulfurous acid, ascorbic acid, fumaric acid, tartaric acid, hydrobromic acid, nitric acid, nitrous acid, hyponitrous acid, disulfuric acid, sulfonic acid, phosphoric acid, pyrophosphoric acid, diphosphonic acid, malonic acid, carbonic acid, succinic acid, carbonic acid, bicarbonic acid, acetic acid, propionic acid, beta alanine, aspartic acid, glutamic acid, leucine, valine, isoleucine, glycine, alanine, proline, phenylalanine, tyrosine, tryptophan, serine, threonine, cysteine, creatine, methionine, asparagine, glutamine.

Further implementations are within the claims.

EXAMPLES

The present disclosure is further illustrated by the following examples that should not be construed as limiting.

1. Production of Acetyl-L-Carnitine Nitrate: Version 1

Acetic acid (96 g) was added to a reaction vessel where it was stirred with L-carnitine (32 g) until L-carnitine was completely dissolved. Acetic anhydride (61.5 g) was then added to the reaction vessel followed by heating the reaction vessel to 80° C. Acetic anhydride and L-carnitine were allowed to reaction for 12 hours to produce acetyl-L-carnitine free base and acetic acid. Once the reaction was completed, acetic acid was removed from the reaction vessel by distillation under a vacuum (−0.09 Mpa) at a temperature below 80° C. The reaction vessel was cooled to about 40° C., and acetone (160 g) was added to the reaction vessel and stirred for about half an hour. The reaction vessel was cooled to below 5° C. to allow the acetyl-L-carnitine free base to crystallize. The reaction vessel was maintained at temperatures between 0° C. to 5° C. for two hours. The acetyl-L-carnitine free base crystals were isolated by filtration, and then washed with acetone. The acetyl-L-carnitine free base crystals were then dried in a vacuum (−0.09 Mpa) at 80° C. The reaction retrieved 36 g of acetyl-L-carnitine free base, which was a yield of 88.9%.

To make acetyl-L-carnitine nitrate salts, the prepared acetyl L-carnitine free base (20.5 g) was dissolved in a reaction vessel with acetic acid (62 g) by stirring. After the acetyl-L-carnitine free base was completely dissolved, reaction vessel was heated to 60° C. and nitric acid (14.5 g) was added to the reaction vessel. The temperature of the reaction vessel was then warmed to 80° C. The nitric acid and the acetyl-L-carnitine free base were allowed to react at 80° C. for 5 hours before the produced acetic acid was removed by distillation in a vacuum (−0.09 Mpa) at a temperature below 80° C. The reaction vessel was then cooled to 40° C. before acetone (102 g) was added and thoroughly stirred with the content of the reaction vessel. The temperature of the reaction vessel was then cooled to below 5° C. to crystallize the acetyl-L-carnitine nitrate. The reaction vessel was maintained at between 0° C. to 5° C. for 2 hours before the acetyl-L-carnitine nitrate crystals were isolated by filtration and washed with acetone. The acetyl-L-carnitine nitrate crystals were dried in a vacuum (−0.09 Mpa) at 80° C. The reaction produced 24.5 g of acetyl-L-carnitine nitrate (92.1% yield).

2. Production of Acetyl-L-Carnitine Nitrate: Version 2

Acetic acid (200 g) was added to a reaction vessel where it was stirred with L-carnitine (130 g) until L-carnitine was completely dissolved. Acetic anhydride (166 g) was then added to the reaction vessel followed by heating the reaction vessel to 30° C. Acetic anhydride and L-carnitine were allowed to reaction for 3 hours to produce acetyl-L-carnitine free base and acetic acid. Once the reaction was completed, acetic acid was removed from the reaction vessel by distillation under a vacuum (−0.09 Mpa) at a temperature below 30° C. The temperature of the reaction vessel was raised to 40° C., and acetone (260 g) was added to the reaction vessel and stirred for about half an hour. The reaction vessel was cooled to below 5° C. to allow the acetyl-L-carnitine free base to crystallize. The reaction vessel was maintained at temperatures between 0° C. to 5° C. for two hours. The acetyl-L-carnitine free base crystals were isolated by filtration, and then washed with acetone. The acetyl-L-carnitine free base crystals were then dried in a vacuum (−0.09 Mpa) at 80° C. The reaction retrieved 147 g of acetyl-L-carnitine free base, which was a yield of 89.2%.

To make acetyl-L-carnitine nitrate salts, the prepared acetyl L-carnitine free base (147 g) was dissolved in a reaction vessel with acetic acid (220 g) by stirring. After the acetyl-L-carnitine free base was completely dissolved, reaction vessel was heated to 30° C. and nitric acid (105 g) was added to the reaction vessel. The temperature of the reaction vessel was then warmed to 30° C. The nitric acid and the acetyl-L-carnitine free base were allowed to react at 30° C. for 2 hours before the produced acetic acid was removed by distillation in a vacuum (−0.09 Mpa) at a temperature about 30° C. Acetone (294 g) was added and thoroughly stirred with the content of the reaction vessel at 30° C. The temperature of the reaction vessel was then cooled to below 5° C. to crystallize the acetyl-L-carnitine nitrate. The reaction vessel was maintained at between 0° C. to 5° C. for 2 hours before the acetyl-L-carnitine nitrate crystals were isolated by filtration and washed with acetone. The acetyl-L-carnitine nitrate crystals were dried in a vacuum (−0.09 Mpa) at 70° C. The reaction produced 177 g of acetyl-L-carnitine nitrate (92.4% yield).

3. Production of Propionyl-l-Carnitine Nitrate

In a reflux flask, L-carnitine base (0.1 moles) and propionic anhydride (0.15 moles), a trace of pyridine, and KOH (0.1 moles) were added. The compounds were gently refluxed at about 80° C. for 1 to 3 hours to produce propionyl-L-carnitine free base and potassium propionate precipitate, which is formed from the propionic acid produced by the reaction react with KOH. Potassium propionate is filtered out of the solution. The isolated propionyl-L-carnitine free base is reacted with nitric acid at a reaction temperature of about 30° C. for 2 hours to produce propionyl-L-carnitine nitrate. The reaction is dried under vacuum to result in pure propionyl-L-carnitine nitrate crystals.

4. Production of Propionyl-l-Carnitine Nitrate with Catalyst

In a reflux flask, L-carnitine base (0.1 moles) and propionic anhydride (0.15 moles), a trace of pyridine, KOH (0.1 moles), and a small amount of pyridine were added. The compounds were gently refluxed for an hour at about 80° C. to produce propionyl-L-carnitine free base and potassium propionate precipitate, which is formed from the propionic acid produced by the reaction react with KOH. Potassium propionate is filtered out of the solution. The isolated propionyl-L-carnitine free base is reacted with nitric acid at a reaction temperature of about 30° C. for 2 hours to produce propionyl-L-carnitine nitrate. The reaction is dried under vacuum to result in pure propionyl-L-carnitine nitrate crystals. The reaction produced 25.2 g of propionyl-L-carnitine nitrate (90.3% yield).

Unless defined otherwise, all technical and scientific terms herein have the same meaning as commonly understood by one of ordinary skill in the art. Although any methods and materials, similar or equivalent to those described herein, can be used in practice or testing, the methods and materials are described herein. The contents of all references, patents, and published patent applications cited throughout this application, as well as the Figures, are incorporated herein by reference in their entirety for all purposes.

The publications discussed herein are provided solely for their disclosure prior to the filing date of the present application. Nothing herein is to be construed as an admission that the present disclosure is not entitled to antedate such publication by virtue of prior invention.

It is understood that this disclosure is not limited to the particular methodology, protocols and materials described as these can vary. It is also understood that the terminology used herein is for the purposes of describing particular implementations only and is not intended to limit the scope of this disclosure, which will be limited only by the appended CLAIMS.

Those skilled in the art will recognize, or be able to ascertain using no more than routine experimentation, many equivalents to the specific implementations described herein. Such equivalents are intended to be encompassed by the CLAIMS.

The invention claimed is:

1. A method of producing acetyl-L-carnitine nitrate comprising:
    reacting L-carnitine with acetic anhydride to produce acetyl-L-carnitine free base;
    isolating the acetyl-L-carnitine free base;
    reacting the acetyl-L-carnitine free base with nitric acid to produce acetyl-L-carnitine nitrate; and
    isolating the acetyl-L-carnitine nitrate,
    wherein reacting L-carnitine with acetic anhydride to produce acetyl-L-carnitine free base comprises dissolving the L-carnitine in acetic acid, and wherein the reaction between L-carnitine and acetic anhydride occurs at a temperature of between 30° C. and 80° C.

2. The method of claim 1, wherein the ratio of acetic acid to L-carnitine is about 0.65 g to 3 g acetic acid for every gram of L-carnitine.

3. The method of claim 1, wherein the reaction between L-carnitine and acetic anhydride occurs for 3 to 12 hours.

4. The method of claim 1, wherein isolating the acetyl-L-carnitine free base comprises:
    distilling the reaction of L-carnitine free base and acetyl anhydride to remove the other products of the reaction;
    washing the acetyl-L-carnitine free base with acetone; and
    crystallizing the acetyl-L-carnitine free base.

5. The method of claim 4, wherein distilling the reaction of L-carnitine and acetic anhydride occurs at reduced pressure.

6. The method of claim 5, wherein distilling the reaction of L-carnitine and acetic anhydride occurs in a vacuum.

7. The method of claim 5, wherein washing the acetyl-L-carnitine free base with acetone comprises using an amount of acetone by grams that is two to five times the amount L-carnitine by grams.

8. The method of claim 5, wherein crystallizing the acetyl-L-carnitine free base comprises cooling the acetyl-L-carnitine free base to below 5° C.

9. The method of claim 8, wherein crystallizing the acetyl-L-carnitine free base further comprises maintaining the acetyl-L-carnitine free base at between 0° C. and 5° C. for at least 2 hours.

10. The method of claim 1, wherein reacting the acetyl-L-carnitine free base with nitric acid to produce acetyl-L-carnitine nitrate comprises dissolving the acetyl-L-carnitine in acetic acid, wherein the reaction between L-carnitine and acetic anhydride occurs at a temperature of between 30° C. and 80° C.

11. The method of claim 10, wherein the ratio of acetic acid to acetyl L-carnitine free base is about 0.8 g to 3 g acetic acid for every gram of acetyl-L-carnitine free base.

12. The method of claim 10, wherein the reaction between the acetyl-L-carnitine free base and nitric acid occurs for about 2 to 5 hours.

13. The method of claim 1, wherein isolating the acetyl-L-carnitine nitrate comprises:
    distilling the reaction of acetyl-L-carnitine free base and nitric acid to remove the other products of the reaction;
    washing the acetyl-L-carnitine nitrate with acetone; and
    crystallizing the acetyl-L-carnitine nitrate.

14. The method of claim 13, wherein washing the acetyl-L-carnitine nitrate with acetone comprises using an amount of acetone by weight that is two to five times the amount acetyl-L-carnitine free base by weight.

15. The method of claim 13, wherein crystallizing the acetyl-L-carnitine nitrate comprises cooling the acetyl-L-carnitine nitrate to below 5° C.

16. The method of claim 15, wherein crystallizing acetyl-L-carnitine nitrate further comprises maintaining the acetyl-L-carnitine nitrate at between 0° C. and 5° C. for at least 2 hours.

17. A method of producing propionyl-L-carnitine nitrate comprising:
    reacting L-carnitine with propionic anhydride to produce propionyl-L-carnitine free base;
    isolating the propionyl-L-carnitine free base;
    reacting the propionyl-L-carnitine free base with nitric acid to produce propionyl-L-carnitine nitrate; and
    isolating the propionyl-L-carnitine nitrate.

18. The method of claim 17, wherein the molar ratio of propionic anhydride to L-carnitine is about 1.5:1.

19. The method of claim 17, wherein reacting L-carnitine with propionic anhydride to produce propionyl-L-carnitine free base further comprises mixing the L-carnitine with potassium hydroxide, wherein the reaction of L-carnitine, potassium hydroxide, and propionic anhydride occurs at a temperature of about 80° C.

20. The method of claim 19, wherein the molar ratio of L-carnitine and potassium hydroxide is 1:1.

21. The method of claim 19, wherein a small amount of pyridine is added to the reaction of L-carnitine, potassium hydroxide, and propionic anhydride as a catalyst.

22. The method of claim 21, wherein the reaction of L-carnitine, potassium hydroxide, and propionic anhydride occurs for between 1 to 3 hours.

23. The method of claim 17, wherein the reaction between the propionyl-L-carnitine free base with nitric acid occurs at about 30° C.

24. The method of claim 23, wherein the reaction between the propionyl-L-carnitine free base and nitric acid occurs for about 2 hours.

25. The method of claim 17, wherein isolating the propionyl-L-carnitine nitrate comprises crystallizing the propionyl-L-carnitine nitrate by drying the reaction between the propionyl-L-carnitine free base and nitric acid.

26. The method of claim 25, wherein the reaction between the propionyl-L-carnitine free base and nitric acid is dried in a vacuum.

27. The method of claim 17, wherein isolating the propionyl-L-carnitine comprises:
  filtering the reaction of L-carnitine and propionic anhydride to discard the precipitate; and
  crystallizing the propionyl-L-carnitine free base.

28. The method of claim 27, wherein crystallizing the propionyl-L-carnitine free base comprises cooling the solution product of the reaction of L-carnitine and propionic anhydride to between 0° C. and 5° C.

* * * * *

UNITED STATES PATENT AND TRADEMARK OFFICE
CERTIFICATE OF CORRECTION

PATENT NO. : 9,573,883 B2
APPLICATION NO. : 14/570748
DATED : February 21, 2017
INVENTOR(S) : Ronald Kramer and Alexander Nikolaidis Page 1 of 1

It is certified that error appears in the above-identified patent and that said Letters Patent is hereby corrected as shown below:

In the Specification

Column 2 Lines 21-24 reads:

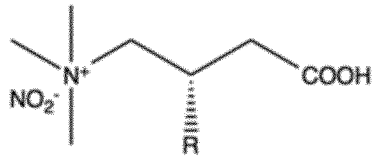

Should read:

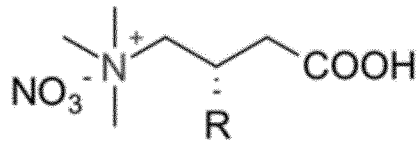

Column 8 Lines 16-19 reads:

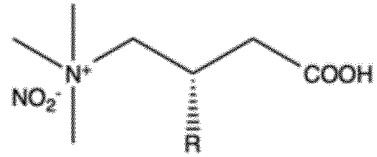

Should read:

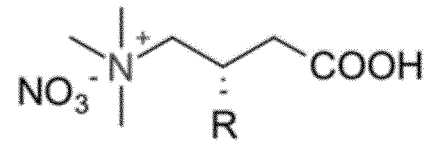

Signed and Sealed this
Fourth Day of August, 2020

Andrei Iancu
*Director of the United States Patent and Trademark Office*